(12) United States Patent
Taylor et al.

(10) Patent No.: US 6,309,851 B1
(45) Date of Patent: *Oct. 30, 2001

(54) METHOD FOR PRODUCING A RECOMBINANT PROTEIN

(75) Inventors: Ronald K. Taylor, Lebanon, PA (US); Joel A. Peek, Pittsford, NY (US)

(73) Assignee: The University of Tennessee Research Corporation, Knoxville, TN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/997,683

(22) Filed: Mar. 19, 1998

Related U.S. Application Data

(63) Continuation of application No. 08/372,951, filed on Jan. 17, 1995, now Pat. No. 5,786,166, which is a continuation-in-part of application No. 07/782,113, filed on Oct. 25, 1991, now Pat. No. 5,382,660.

(51) Int. Cl.[7] .................................................. C12Q 1/26
(52) U.S. Cl. ............................................. 435/25; 435/69.1
(58) Field of Search ................................. 435/172.1, 243, 435/252.1, 252.3, 69.1

(56) References Cited

U.S. PATENT DOCUMENTS 5,382,660 * 1/1995 Taylor et al. ...................... 536/23.2

OTHER PUBLICATIONS

Peterson et al., Infection and Immunity, 1988, vol. 56, pp. 2822–2829.*
Peek et al., PNAS, 1992, vol. 89, pp. 6210–6214.*
Tomb et al., PNAS, 1992, vol. 89, pp. 10252–10256.*
Bardwell et al., Cell, 1991, vol. 67, pp. 581–589.*

* cited by examiner

Primary Examiner—Ponnathapu Achutamurthy
Assistant Examiner—Kathleen Kerr
(74) Attorney, Agent, or Firm—Schnader Harrison Segal & Lewis LLP

(57) ABSTRACT

A method to inhibit the function of a class of bacterial periplasmic oxidoreductase enzymes, exemplified by TcpG of *Vibrio cholerae*, DsbA of *E. coli*, and Por of *Haemophilus influenzae*, is disclosed. A screening method to determine whether a chemical inhibits the function of the oxidoreductase enzymes is disclosed. Mutant bacteria lacking the ability to produce a functional periplasmic oxidoreductase and a cloned expression vector overproducing TcpG are also disclosed.

18 Claims, 14 Drawing Sheets

METHOD FOR PRODUCING A RECOMBINANT PROTEIN

Figure 1:
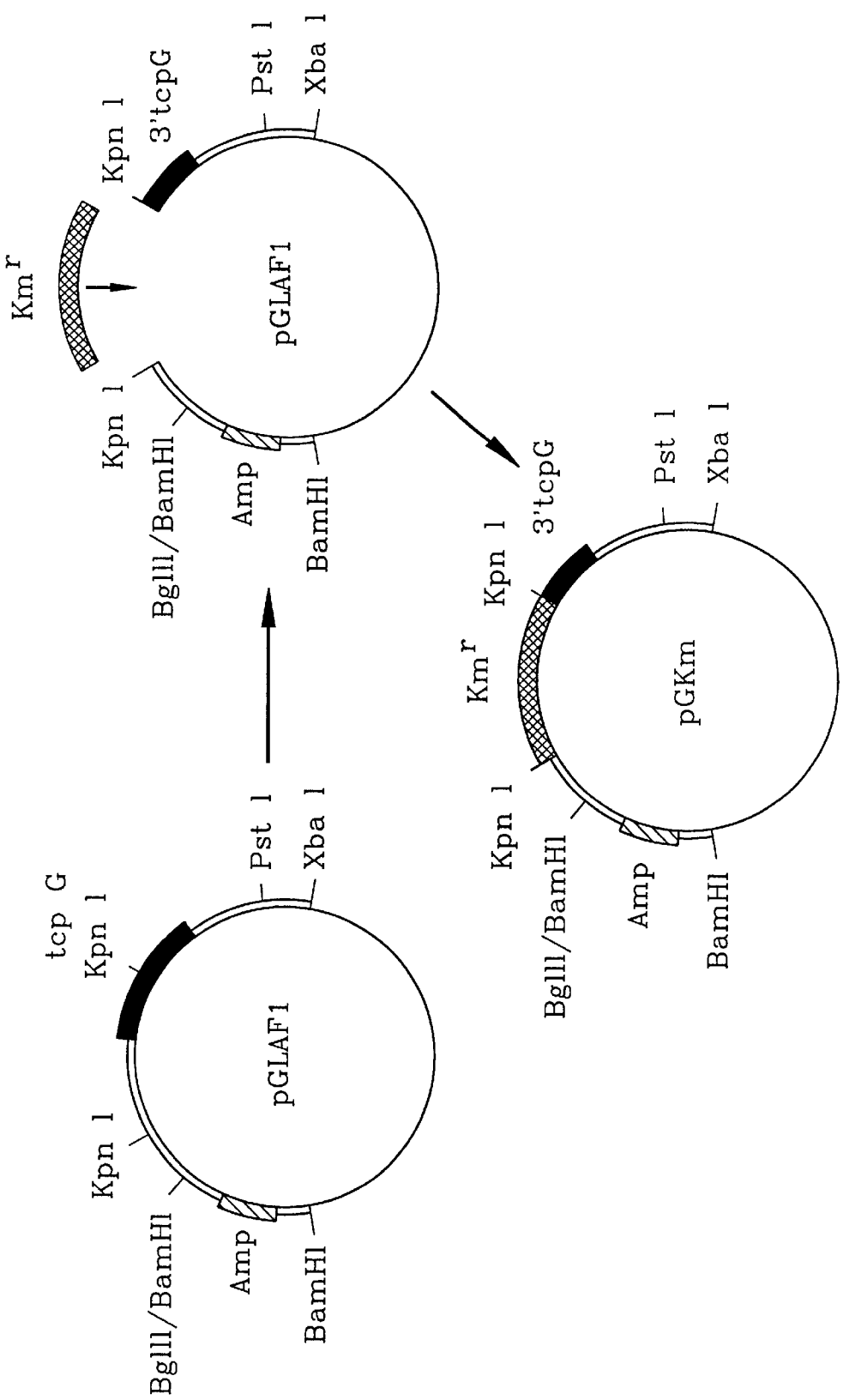
Figure 2:
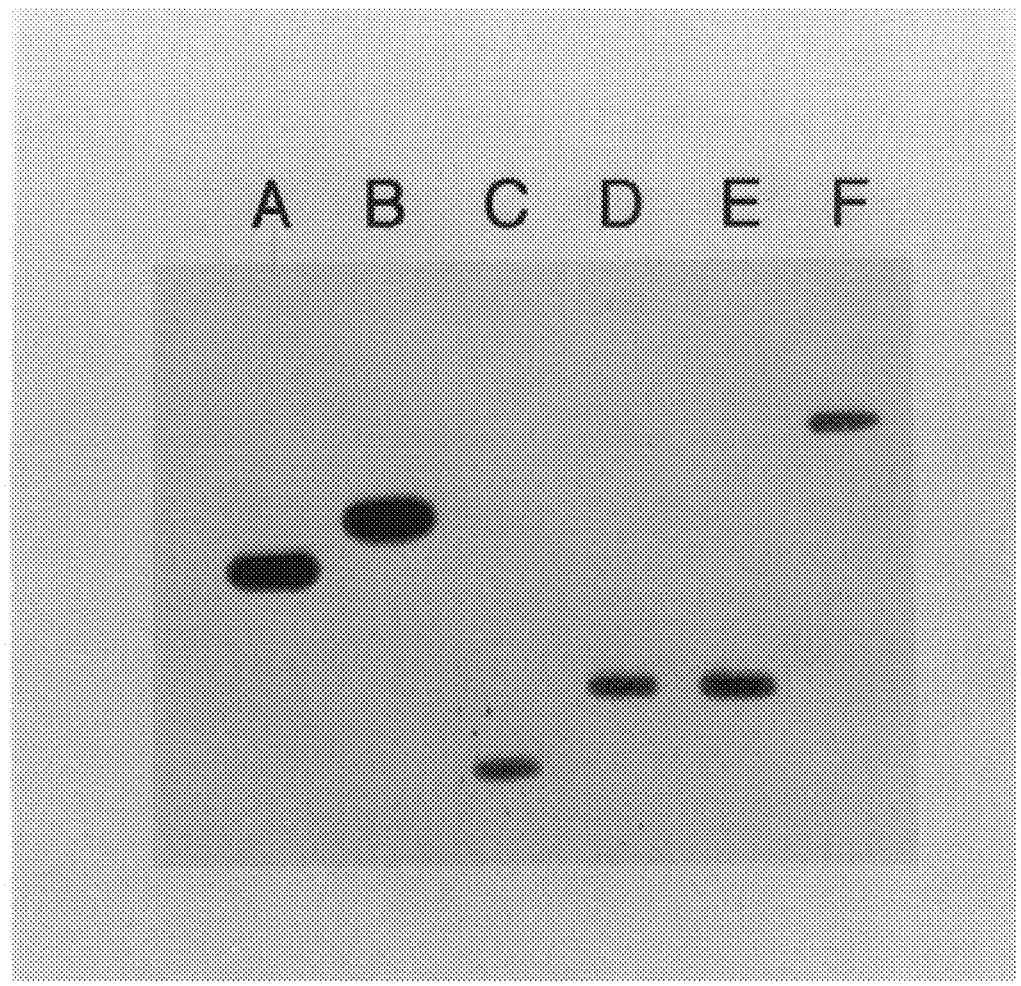
Figure 3:
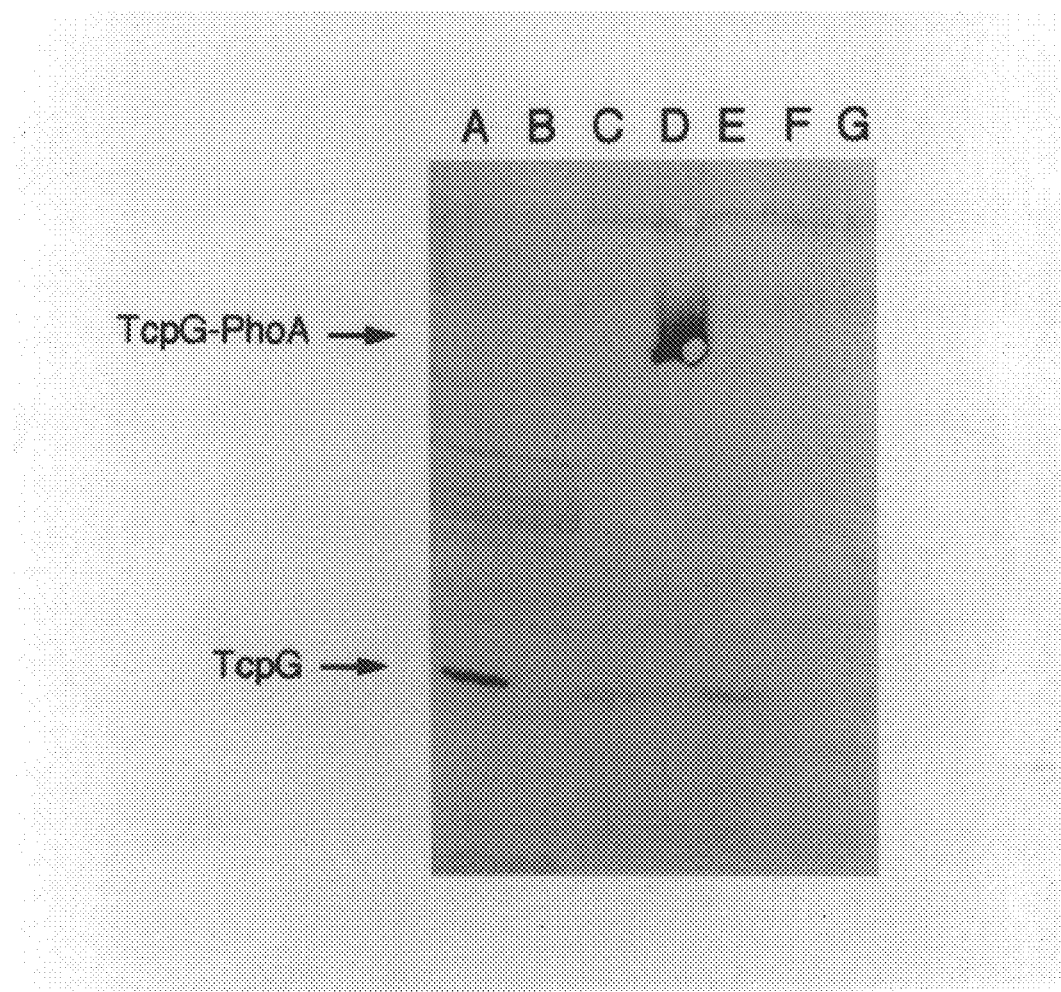
Figure 4:
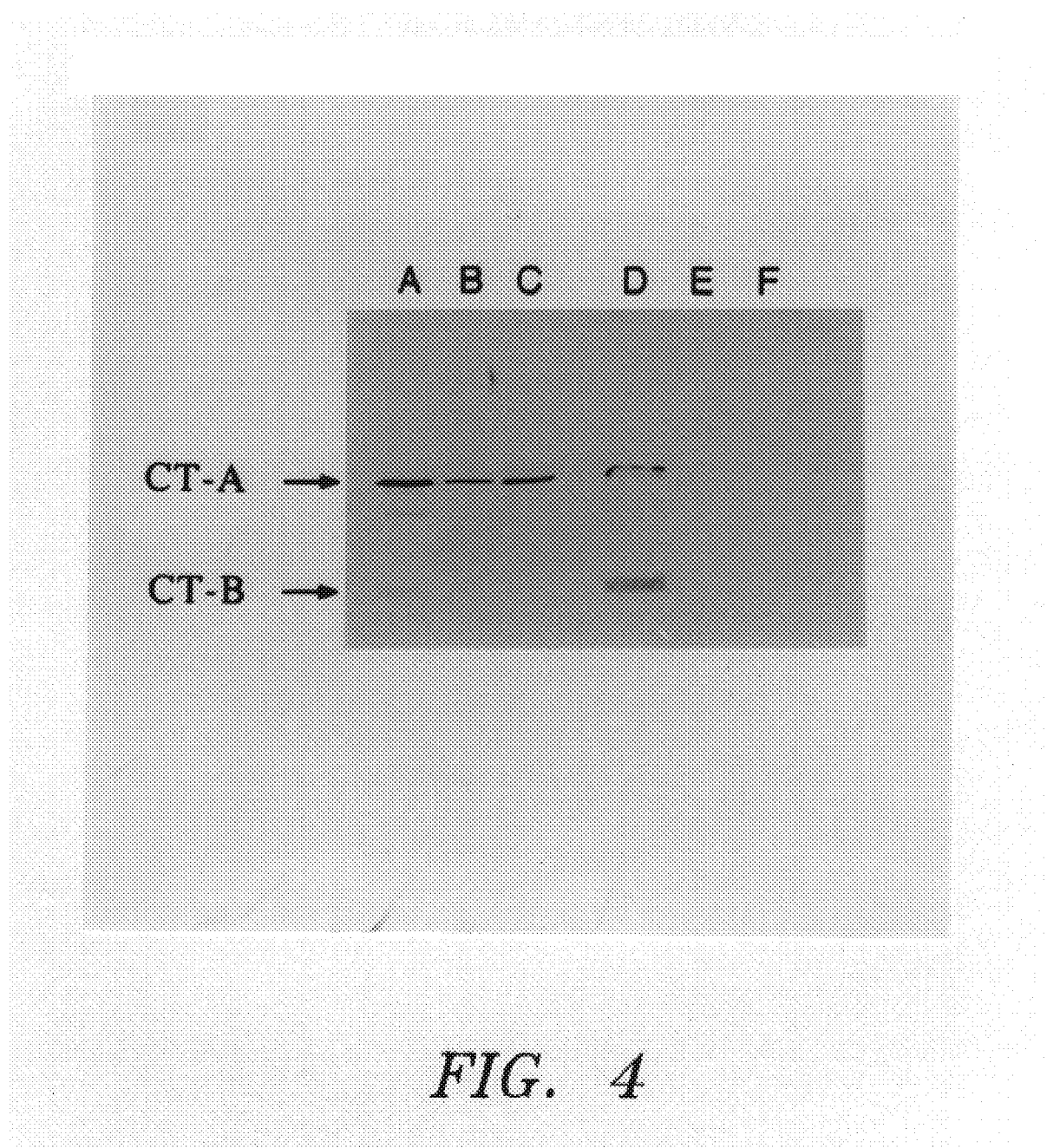
Figure 5:
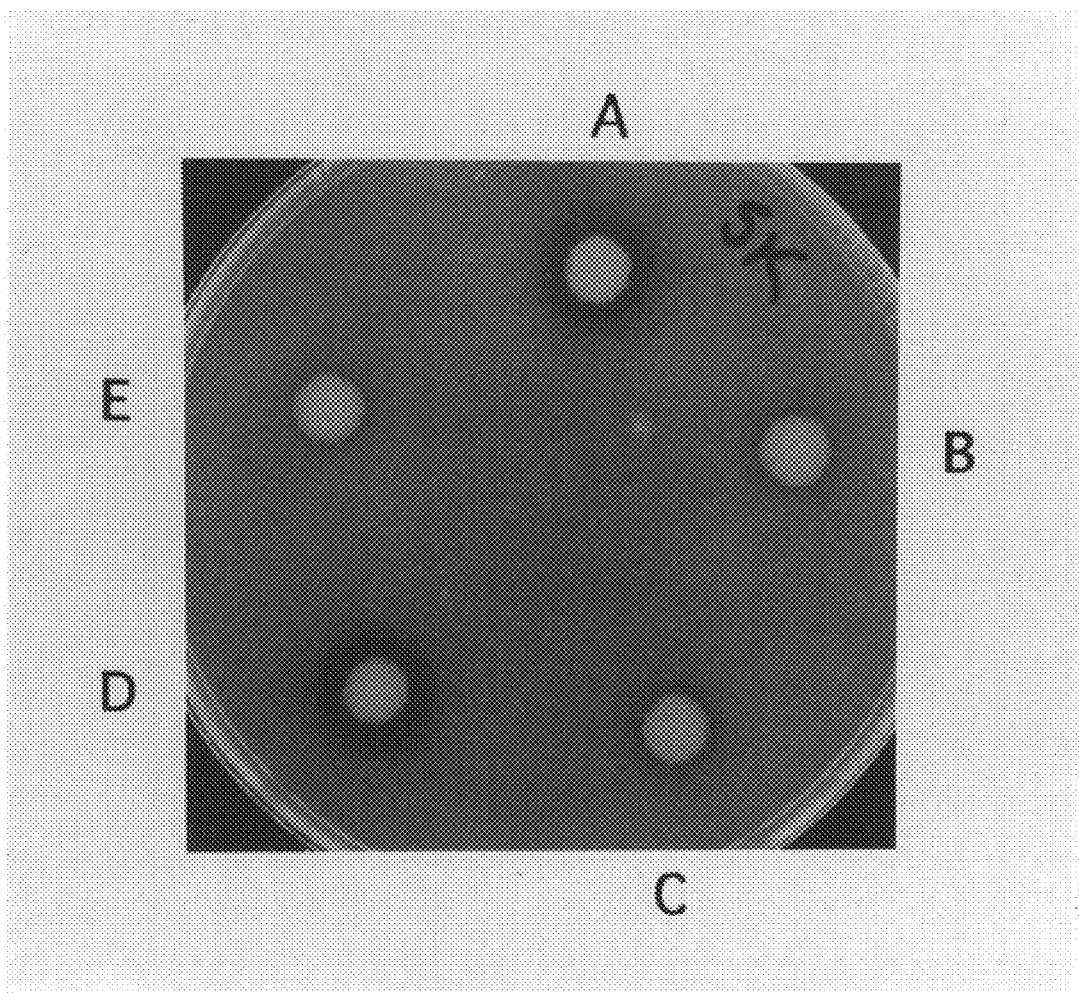
Figure 6:
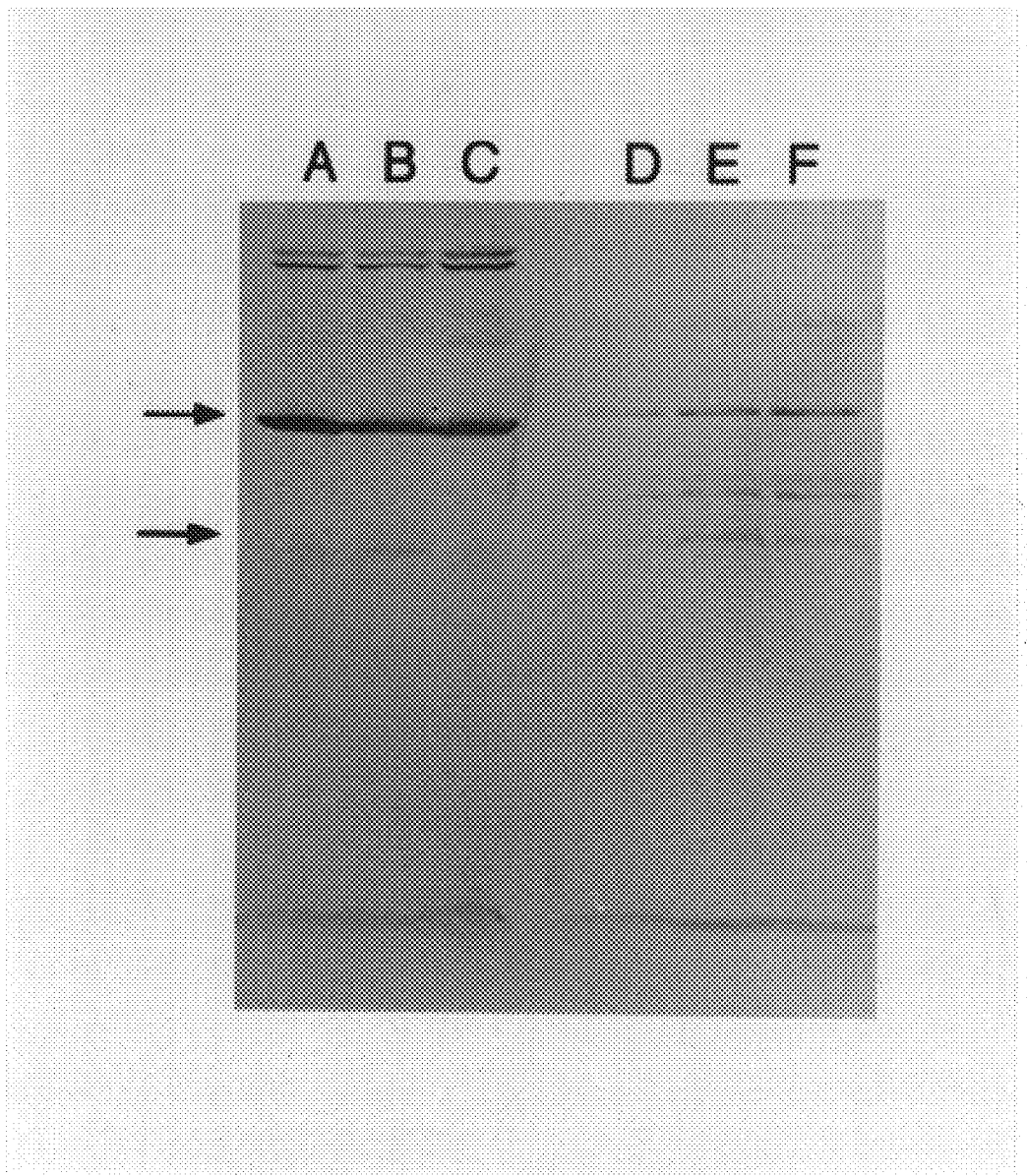
Figure 7:
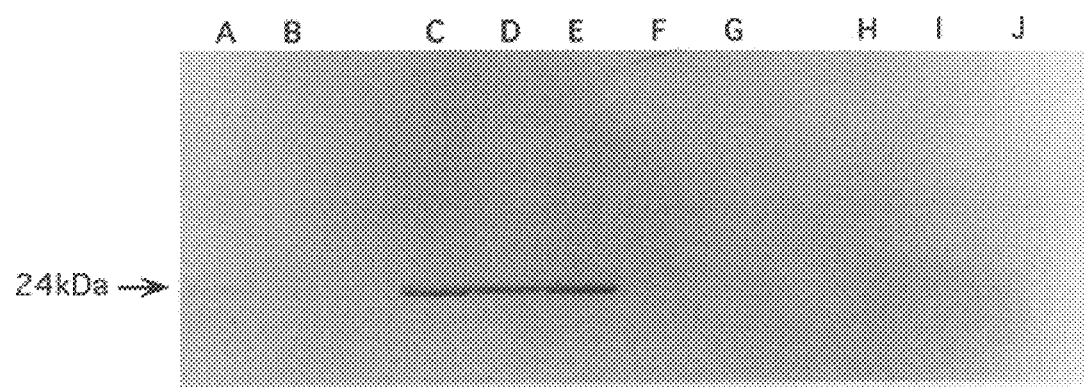
Figure 8A:
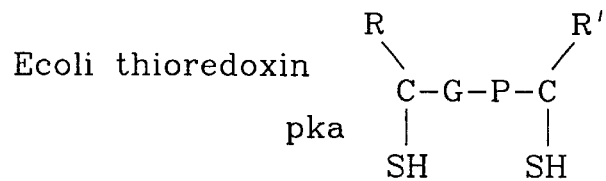
Figure 8B:
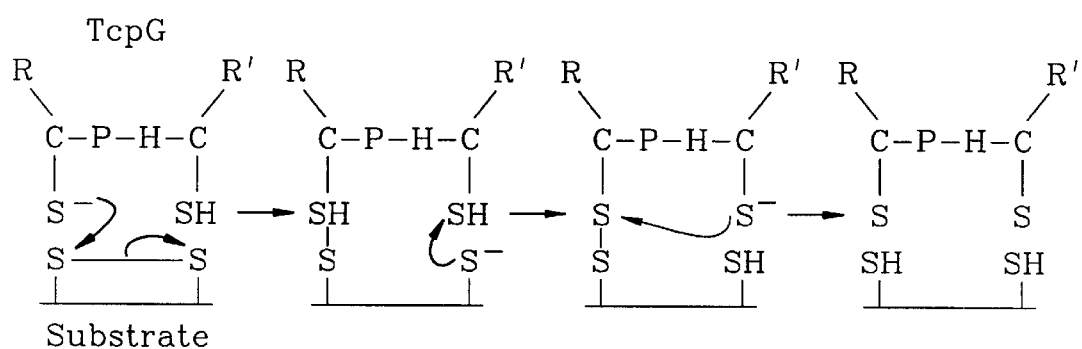
Figure 8C:
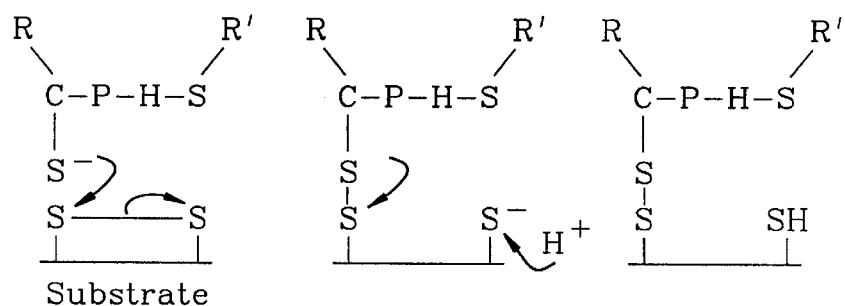
Figure 9:
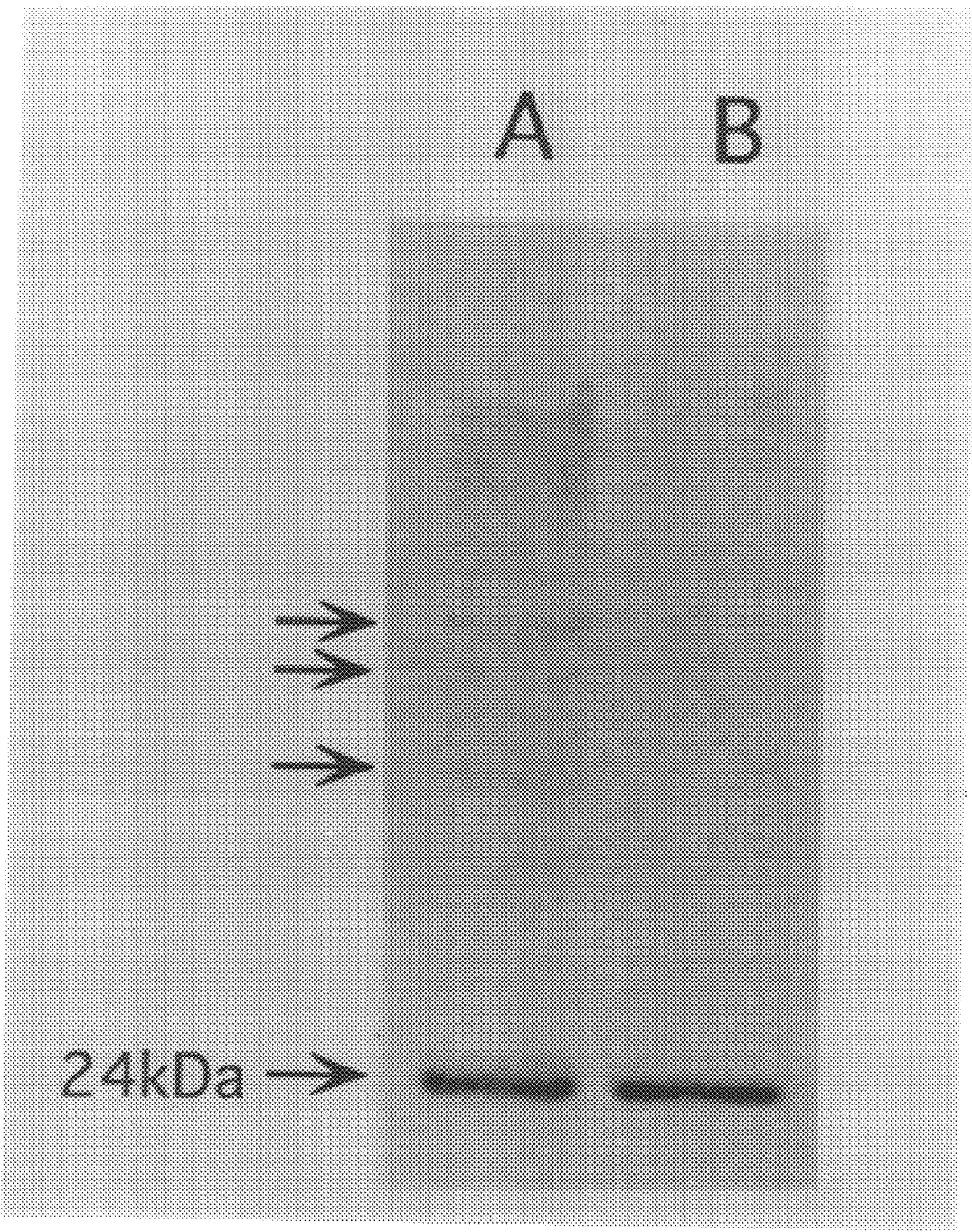
Figure 10:
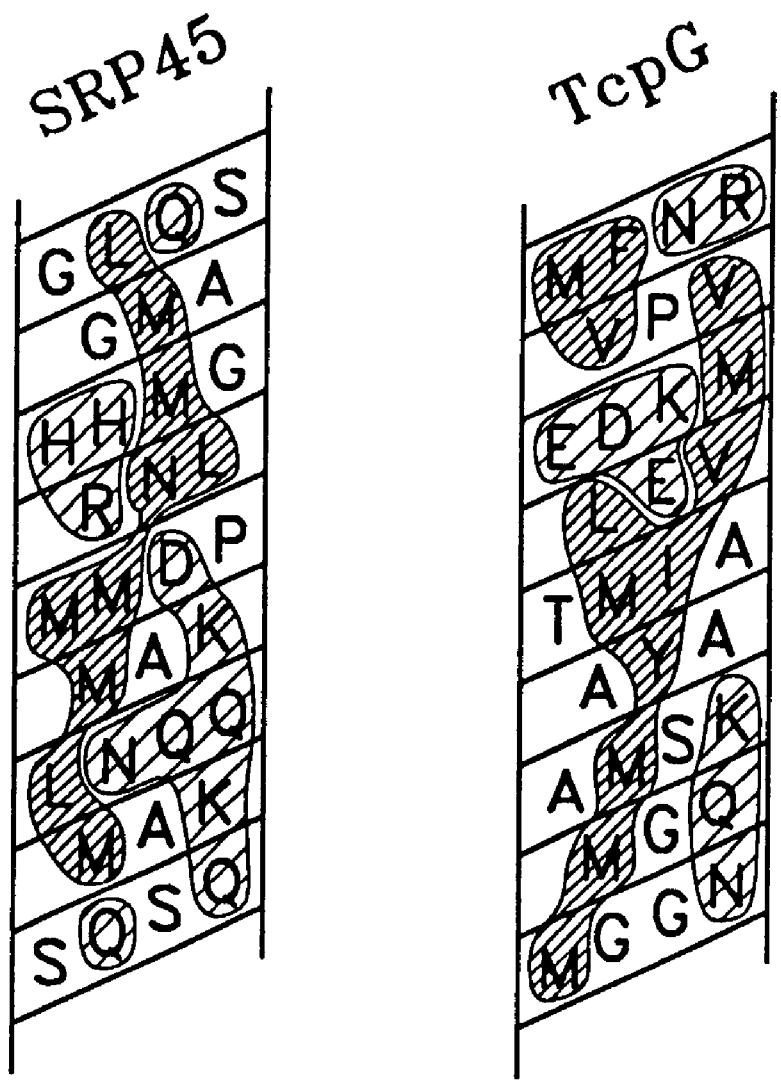
Figure 11:
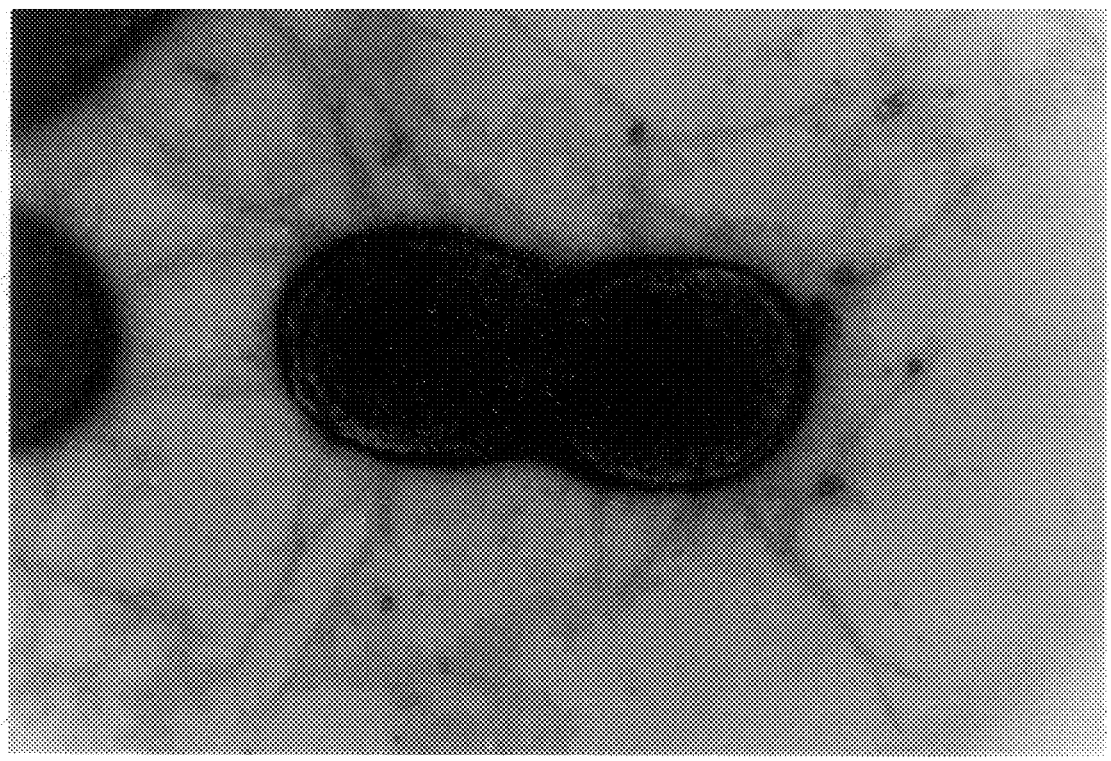
Figure 12:
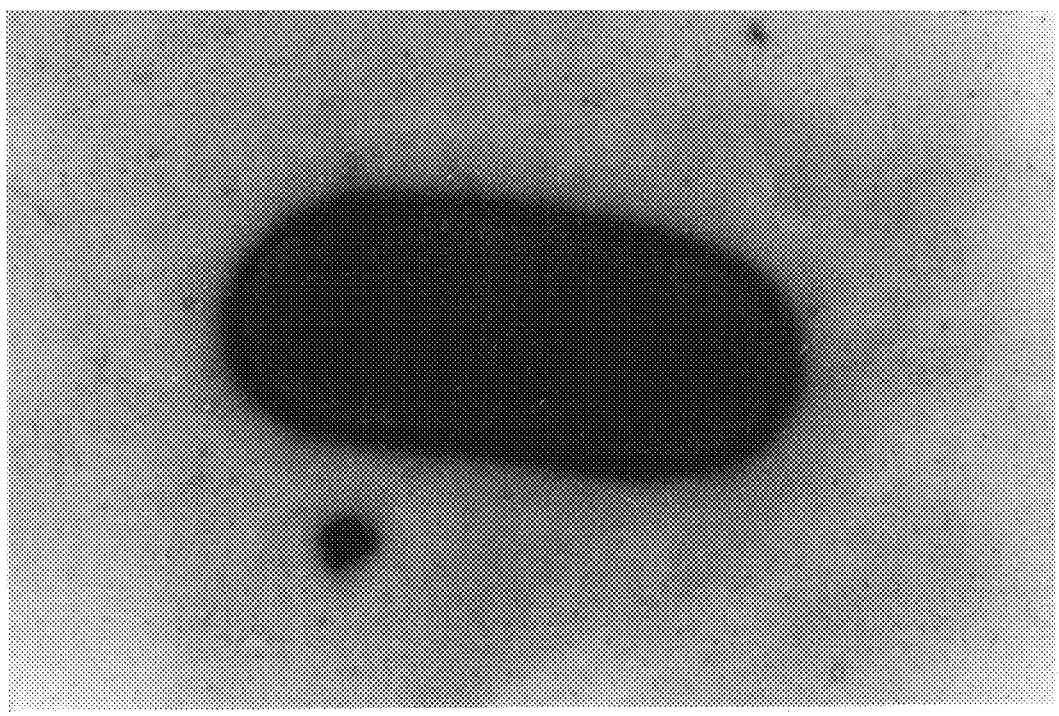
Figure 13:

This application is a continuation of U.S. patent application Ser. No. 08/372,951 filed Jan. 17, 1995 (now U.S. Pat. No. 5,786,166) which is a continuation-in-part of U.S. patent application Ser. No. 07/782,113 filed Oct. 25, 1991 (now U.S. Pat. No. 5,382,660).

The present invention was developed, in part, with funds from the United States Public Health Service (Grant AI-25096) and the National Institutes of Health (Grant AI-07238). The United States Government has certain rights in the present invention.

BACKGROUND

Bacteria, as is known, are the causative agents for a great many diseases in animals and humans. Before the advent of antibiotics, such as penicillin, bacterial infections were considered to be non-treatable. Since that time, however, the fight against bacterial diseases has often appeared to be won as antibiotic after antibiotic proved effective to combat the diseases and the bacteria that caused them.

Recently, however, bacterial diseases such as meningitis, pneumonia, tuberculosis, and enterotoxic diseases are on the increase due to the proliferation of antibiotic resistant strains of pathogenic bacteria. Bacterial resistance occurs because antibiotic therapy naturally kills most easily and swiftly the bacteria which are most sensitive to the antibiotic, leaving behind the bacteria which are less affected by the antibiotic therapy. Additionally, certain bacteria can pass antibiotic resistance genes to other otherwise sensitive bacteria. Over time, the populations of antibiotic sensitive bacteria disappear leaving only resistant populations.

This problem has been noted in scientific and popular articles, such as Begley, "The End of Antibiotics", Newsweek, Mar. 28, 1994, pages 47–52 ("Begley"), and Science, vol. 264, Apr. 15, 1994, the entire issue of which is dedicated to the problem of microbial resistance to antibiotics. Begley and Science vol. 264 are incorporated herein by reference.

Science has responded by discovering newer and better antibiotics with which to treat resistant bacteria. However, it appears that, as fast as new antibiotics can be produced, resistant strains of bacteria develop. Therefore, there is a clear and pressing need for new molecules and new means of treating bacterial infections.

Bacteria capable of producing disease in plants and animals, especially mammals, such as humans, and porcine, bovine, ovine, caprine, equine, feline, and canine species, such as pigs, cattle, sheep, goats, horses, cats, and dogs, require the production of certain proteins, known as virulence factors, or virulence determinants, to produce disease. That is, the bacteria are avirulent unless the virulence determinants are produced in an active form. Examples of virulence determinants include toxins, proteolytic enzymes, and structures such as pili which are required for adherence of the bacteria to tissues of the host organism. These virulence determinant proteins are generally secreted products, that is they are present on bacterial cell surfaces or are secreted totally outside of the bacterial cell. These exported virulence determinants pass through the bacterial periplasm on their way to their final location on or outside of the cell.

As taught in the parent application, a class of periplasmic bacterial oxidoreductase enzymes illustrated by the enzyme TcpG, have been discovered which function to catalyze the formation of disulfide bonds. The formation of these bonds allows the virulence determinant proteins to assume a functional, stable three dimensional conformation. Conversely, without these bonds, and the resulting active conformation, the virulence determinants are inactive. A major proportion of the teachings of the parent application has been published in a recent article by the inventors entitled "Characterization Of A Periplasmic Thiol:Disulfide Interchange Protein Required For The Functional Maturation Of Secreted Virulence Factors Of Vibrio Cholerae", PNAS; 89:6210–6214 (1992). This article is incorporated by reference and is cofiled with the present application as an integral part of this application.

The parent application teaches that preventing a microorganism from producing its oxidoreductase enzyme results in the production of inactive virulence determinants due to the lack of active 3-dimensional conformation. The parent application presents data showing that the lack of the periplasmic oxidoreductase enzyme TcpG in mutant Vibrio cholerae is responsible for failure of the mutants to produce active virulent cholera toxin.

In accordance with the invention, this application presents further data, set forth in an unpublished manuscript by the inventors entitled, "The Catalytic Site of Vibrio cholerae TcpG Disulfide Isomerase is Required for the Extracellular Localization or Function of a Variety of Secreted Virulence Factors." Further study has been made relating to the oxidoreductases' role in and relationship to te production of virulence determinant proteins and their symptoms. It has been found that the failure to produce active PcpG is responsible for the failure to produce active virulence determinant proteins, the effect of lack of TcpG is pleitropic, causing various effects on numerous virulence determinants which contain disulfide bonds, and that by providing active TcpG to bacteria incapable of producing TcpG, and therefore to produce inactive virulence determinant proteins.

There have also been developed several tests, in addition to the procedures taught in the parent application, to determine whether virulence determinants of a bacteria are active or inactive by measuring the symptoms thereof. By site-directed mutations that result in changing specific amino acids, the active site of the TcpG protein can be identified.

Periplasmic proteins with homologous structure and function to TcpG have been identified in other bacterial species, for example the DsbA protein in *E. coli* and the Por protein in *Haemophilus influenzae*, and similar homologous proteins identified in *Salmonella typhimurium, Bacillus brevis*, Legionella, and the plant pathogen *Erwinia chrysanthemi*. The identification of POREs in Bacillus suggests that POREs are likely present in other gram positive bacteria such as streptococcus and staphylococcus, important pathogens in humans and other animal species. These proteins, as well as other homologous proteins, already discovered or to be discovered in other bacterial species, are referred to collectively in this application as periplasmic oxidoreductase enzymes ("PORE"). However, neither the relationship of these PORE to the activity of virulence determinant proteins nor methods to inhibit the formation of active virulence determinant proteins by inhibition of the function of POREs have previously been disclosed.

Because of the extensive homology of structure and function of these proteins, it is believed, in accordance with the present invention, that observations related to structure and function.which are applicable to one member of the bacterial PORE family are applicable to all PORES. It has been discussed, for example, as described below, preventing the expression of the DsbA gene of *E. coli* results in the inability of the bacteria to produce an active pilus, rendering the bacteria avirulent. Likewise, preventing the expression of the TcpG gene in *V. cholerae* results in an avirulent bacteria with a morphologically normal but non-functional pilus.

Thus, it became apparent that inhibition of the function of POREs ultimately results in death of a pathogenic bacterium in vivo because of the failure of the organism to perform an essential function, such as the ability to colonize the intestinal wall.

Unlike antibiotics, however, inhibition of POREs does not result in lysis of the bacterial cell, which can contribute to the release of further endotoxins and exacerbate endotoxic shock as can occur in *E. coli* septicemia, for example.

The invention contributes to solving the serious problem of bacterial resistance to antibiotics. The invention provides a method for screening for and finding new antibacterial compounds which attack bacteria in previously unknown ways. The POREs taught herein represent a novel antibacterial drug target because, for one thing, until recently, POREs were not known to exist. Unlike most current antibiotics, which target the bacterial ribosomal protein synthesis apparatus or inhibit the formation of a functional bacterial cell wall, POREs are located in the periplasm and promote the production of active virulence determinant proteins. Thus, antibacterial compounds targeting POREs adds a new weapon in the fight against bacteria.

Antibacterial therapies aimed at POREs augments traditional antibiotic therapy because, as discussed below, many bacterial resistance proteins are secreted proteins which require POREs their activity in conferring resistance. It has been discovered that, the activity of bacterial proteins providing resistance to antibiotics, such as β-lactamase which confers resistance to β-lactam antibiotics such as penicillin and ampicillin, requires a functional PORE in order for the bacteria to be resistant to these antibiotics. Thus, the proteins which cause bacterial resistance to antibiotics can be rendered inactive by inhibiting POREs.

Additionally, therapies targeting POREs can be used in conjunction with conventional antibiotics to reduce the development of resistant organisms. The likelihood of developing resistance to multiple therapies aimed at different bacterial targets is much reduced compared with the development of resistance to only one therapeutic compound.

Moreover, it is believed that drugs which will inhibit PORE function are currently available, although their use in relation to PORE is not known. The reason is that, in screening molecules for antibacterial uses, pharmaceutical and biotechnology companies generally look for inhibition of cell growth or death of cells. However, inhibition of POREs in vitro does not inhibit cell growth nor cause cell death, but results in avirulent live cells. Thus, molecules which would be effective against virulent bacteria by inhibiting PORE function might well be missed by standard or conventional assays.

Additional background information is found in the articles listed in the bibliography of this application. The articles are incorporated herein by reference.

SUMMARY OF THE INVENTION

The invention relates to a method for screening molecules for the ability to inhibit bacterial POREs, such as TcpG, DsbA, or Por, from promoting the formation of active virulence determinant proteins.

The method comprises exposing a bacteria, known to secrete a virulence determinant, is exposed to a chemical and determining whether or not one or more symptoms of the virulence determinant proteins is observed. The term "symptom" refers to an observable manifestation. A chemical which adversely affects the PORE enzyme from producing active virulence determinants tests positive when one or more symptoms of the virulence determinant proteins are found to be inactive. Because most virulence determinants contain disulfide bonds, which bonds are formed by the action of POREs, it is necessary only to determine the effect of a chemical on one symptom of virulence determinant to ascertain that the PORE has been adversely affected. If, for instance, pili are not formed, the test for the chemical is positive. Because of the pleiotropic nature of the effect of inhibition of POREs, chemical inhibition of a PORE will have the same result for virtually all virulence determinant proteins, that is, lack of function.

If preferred, additional tests can be performed, as described below, to verify that the loss of function of the virulence determinant was due to inhibition of bacterial PORE.

Additionally, it is necessary to perform these tests on only one species of bacteria known to secrete virulence determinants, such as *V. cholerae* or *E. coli*. Because POREs from different bacteria are highly homologous, both in function and structure, a chemical which adversely affects one bacterial PORE will adversely affect POREs in other bacteria.

Another embodiment of the invention is a method for inhibiting the formation of active bacterial virulence determinant proteins. The method comprises exposing a bacteria, which naturally secretes active virulence factors, to a chemical which inhibits the function of POREs, resulting in the inability of the bacteria to form virulence determinants in active conformation.

In accordance with the invention, it has been determined, in every secreted virulence determinant protein studied, in both human and veterinary pathogens, that loss of active PORE results in the production of inactive virulence determinants. Accordingly, the invention is applicable to human and veterinary pathogens involving all animals, especially mammals, and especially humans and domestic animal species such as pigs, cattle, horses, sheep, goats, dogs, and cats.

Certain mutations to the TcpG result in inactive TcpG, which in turn results in the fornation of nonnal morphologic, but inactive, bacterial virulence determinants.

Hemagglutination, in vivo intestinal growth, and protease activity assays are useful to determine if the virulence determinant proteins of a bacterium such as *V. cholerae* or *E. coli* are active or not. Other assays to determine the activity or inactivity of bacterial virulence determinants have also been developed.

One embodiment of the invention is a method for determining the effect of a compound on the symptoms, active or inactive, of a virulence determinant of a bacterium. By assaying the activity of virulence determinants of a bacteria, one skilled in the art can determine the effect of a compound to which the bacteria has been exposed on the symptoms of bacterial virulence determinants. A bacterium which naturally produces virulence determinants containing disulfide bonds, such as *V. cholerae* or *E. coli*, is first exposed in culture to a test compound. Then, the symptoms of the activity of virulence determinants is assayed using one of the above mentioned assay or any other assay which determines whether or not the virulence determinant is active or inactive. If a virulence determinant is found to be inactivated by the test compound, if desired, one skilled in the art can perform confirmatory tests, to verify that the virulence determinant is defective due to incorrect conformation because of lack of functional oxidoreductase enzyme.

Another embodiment of the invention comprises mutant bacteria incapable of producing active TcpG or other PORE. The procedure to make, and characteristics and uses of, these mutant bacteria are described in the parent application and in the Manuscript.

A further embodiment of the invention is a TcpG overproducing competent self replicating cloned expression vector, which may be a plasmid. These plasmid clones may be used to transform a bacteria, and are useful as source material for TcpG, which can be used as a test model for screening compounds which inactivate TcpG. Compounds which are found to have this property may then be tested on bacteria, as described above, to determine if the compounds are useful to prevent bacteria from producing active virulence determinants proteins. Additionally, the clones are useful to produce TcpG in sufficient quantities to allow for purification of TcpG for biochemical analysis and characterization of TcpG and for studies of the three-dimensional structure of TcpG by x-ray crystallography.

BRIEF DESCRIPTION OF THE FIGURES

FIG. 1 is a schematic representation of production of the plasmid pGKm.

FIG. 2 is a southern blot analysis of a construction prepared according to the method of the present invention.

FIG. 3 is a western blot of a construction prepared according to the method of the present invention.

FIG. 4 is a western blot showing a comparison of 0395, JP100 and KP8-96 cholera toxins.

FIG. 5 is a comparison of protease activity on casein agar.

FIG. 6 is an immuno-blot showing a comparison of O395, JP100 and KP8-96 periplasmic and secreted HA/protease profiles.

FIG. 7 is a western blot localization of mutant TcpG proteins.

FIG. 8 is a schematic of a proposed catalytic mechanism for TcpG.

FIG. 9 is a non-reducing immuno-blot of periplasmic samples using anti-TcpG antibodies.

FIG. 10 is a comparison of projections of amphipathic helix SRP54h3b and the postulated amphipathic helix of TcpG.

FIG. 11 shows a microphotograph of an *E. coli* bacterium, strain K12, which was transfected with plasmid pDMS8 encoding 987P fimbriae. The bacterium is shown expressing Type 1 fimbriae (endogenous) and 987P fimbriae from its surface.

FIG. 12 shows a microphotograph of an *E. coli* bacterium, strain K12 DsbA– mutant containing the same plasmid as the bacterium shown in FIG. 11. Note that no Type 1 or 987P fimbriae are present.

FIG. 13 shows a photograph of a gel following Western blotting using anti-TcpG antibody. Lane 1 is of an *E. coli* carrying cloned TcpG on a plasmid. Lane 2 is of an *E. coli* carrying cloned TcpG on an overproducing plasmid. Lane 3 is of an *E. coli* without a TcpG gene containing plasmid.

FIG. 14 shows a diagrammatic representation of the pTrc99A expression vector into which the TcpG gene is inserted.

DETAILED DESCRIPTION OF PREFERRED EMBODIMENTS OF THE INVENTION

In a first embodiment, the invention provides a method for determining the effect of a test compound on one or more symptom of a virulence determinant of a bacterium. The test compound may be any compound believed to have the ability to interfere with the formation of active bacterial virulence determinants. The compound may be a compound or a chemical known to have other biological effects, such as a medication or an antibiotic, or it may be a compound not known to have biological effects. Preferably, the compound is one that is known to either disrupt the function or formation of POREs or of the virulence determinants themselves.

In a preferred embodiment, dithiothreitol ("DTT") is the chemical to be tested for determination of its effects on the symptoms of bacterial virulence determinants. DTT, also known as Cleland's Reagent, is disclosed in Cleland, W. W., *Biochemistry*, 3:480 (1964).

Bacteria which may be used in the test include any bacteria known to produce virulence determinants having disulfide bonds. *Vibrio cholerae, Escherichia coli*, and *Haemophilus influenzae* are preferred test subject bacterial species.

The bacteria to be tested, for example *V. cholerae*, are grown in culture, which culture medium may be solid or liquid. Various concentrations of the test compound, such as DTT, a chemical known to inhibit the function of POREs, in concentrations between about 1 mM and 20 mM, preferably between about 5 mM and 10 mM, and most preferably about 7.5 mM, are incorporated into the solid culture medium or between 0.01 mM and up to about 0.5 mM, preferably between about 0.05 and 0.1 mM may be introduced into the liquid culture medium, either prior to or after the bacteria are cultured. Preferably, the concentration of the compound is at or above the level at which the compound will inhibit or prevent the formation of active virulence determinants and below the level at which the compound will kill the bacteria.

The bacteria are allowed to remain in contact with the compound for various time periods during which time the bacteria may continue to grow in culture. The time periods may range from immediate removal from the culture medium following exposure to the compound to overnight or several days, for example about two days, following exposure. Preferably, the bacteria are allowed to remain in contact for a time believed to be sufficient for the compound to adversely affect the bacterials ability to form active virulence determinants.

Following the exposure of the bacteria to the compound, the bacteria are tested for one or more symptoms of active virulence determinants. Any test that differentiates between the presence of active or inactive bacterial virulence determinants may be used. A combination of tests may be used. In a preferred mode using *V. cholerae* as the subject bacteria, the bacteria are tested for the ability to perform functions requiring the presence of active virulence determinants, such as the ability to autoagglutinate, to hydrolyze proteins such as casein, or to produce active toxin. *V. cholerae* grown in liquid medium are exposed to the test chemical, such as DTT. The ability of the bacteria to autoagglutinate, a property dependent on the function of an active pilus virulence determinant, is assessed visually by noting the presence or absence of clumping of the bacteria in the liquid medium. Conversely, *V. cholerae* growing on solid medium containing casein can be assessed visually for the ability to digest casein, a property dependent on the presence of active protease virulence determinant.

In another preferred mode using *E. coli* as the subject bacteria, the bacteria are tested for the ability to produce toxin or a functional pilus.

In another preferred mode, the relative sensitivity of a bacteria to ampicillin or other β-lactam antibiotic may be used as a test to determine whether a bacteria produces active PORE, such as TcpG or DsbA. β-lactamase, a protein which confers resistance to β-lactam antibiotics, is a periplasmic protein which contains disulfide bonds, and which requires PORE for its active function. It has been found that mutant bacteria incapable of producing functional TcpG, but otherwise identical to wild type, are less resistant to β-lactam antibiotics, such as ampicillin, than are wild type bacteria.

Further testing may be performed to verify that the failure to perform functions requiring active virulence determinants is indeed due to inability to produce the virulence determinants in a functional form. Because of the pleiotropic nature of the effects of POREs and the diverse nature of the virulence determinants themselves, determining that multiple virulence determinant proteins are inactive as the result of the compound indicates that the loss of activity is due to inactivation of PORE. For example, lack of autoagglutination ability may be followed by testing for protease activity or active toxin production, which virulence determinants are also dependent on PORE. The defective bacteria may be transfected with an overproducing expression vector such as a plasmid carrying a gene encoding an active PORE, such as TcpG, DsbA, or Por. If, upon repeat testing for active virulence determinants after transformation with the overproducing vector, the bacteria are found to have active virulence determinants, it is concluded that the inactivity of the virulence determinant was due to the effect of the test compound on POREs. Other tests, such as electron microscopy or western blotting, can be used to determine if the virulence determinants are present, although non-functional, indicating that the inactivity of the virulence determinants is due to faulty three-dimensional conformation, or not present due to degradation of the misfolded proteins.

Other tests to determine the presence of active or inactive virulence determinants and the cause of the failure to produce active virulence determinants, such as those tests employing mutant bacteria, have been described.

In another embodiment of the invention, mutant bacteria were produced, which bacteria were incapable of producing active virulence determinants due to the inability to produce active PORE. In a preferred mode, the mutant bacteria are *V. cholerae* incapable of producing active TcpG. Examples of procedures for making and using the mutant bacteria are taught in the present application.

A third embodiment of the invention is a cloned expression vector overproducing TcpG. Insertion of the vector into a competent microorganism eukaryote or prokaryote. A transformed bacterium such as can be made to overproduce TcpG or, which can be harvested and used to directly test the ability of chemicals to interfere with the function of TcpG or another pore like DsbA. or Por. The expression vector may be a plasmid. In a preferred embodiment, the plasmid is pTrc99A. (Behringwerke Aktiengesellschaft, Marburg, Germany, GenBank Accession Number U13872).

Other embodiments of the invention are apparent from the teachings herein provided.

The following examples are offered as merely illustrative and the invention is not to be so limited.

EXAMPLE 1

EXPOSING VIRULENT BACTERIA TO TEST MOLECULE

Virulent *V. cholerae* are grown in separate tubes containing liquid LB (Luria-Bertani) culture medium to which DTT, at a concentration of 0.1 mM of culture medium, was added.

Virulent *V. cholerae* are grown on separate plates containing solid LB (Luria-Bertani) agar culture medium to which DTT, at a concentration of 7.5 mM of culture medium, was added.

EXAMPLE 2

TESTING BACTERIA FOR ACTIVE VIRULENCE DETERMINANT PROTEINS

The bacteria are then tested for the presence of active virulence determinants, Additional tests, such as autoagglutination, and toxin secretion, are also performed on the DTT exposed bacteria. All tests performed demonstrate the presence of inactive virulence determinants in the bacteria exposed to DTT, and fail to demonstrate the presence of an active virulence deterninant.

Bacteria in liquid culture medium are tested visually for the ability to autoagglutinate. Bacterial autoagglutination results in visible bacterial clumping within the culture medium. Lack of visible clumping indicates a positive result, that is that the chemical caused the lack of active virulence determinant essential for autoagglutination.

Bacteria in solid culture medium are tested for the ability to hydrolyze casein. Bacteria with active protease virulence determinant will hydrolyze a ring of casein surrounding the bacterial culture.

EXAMPLE 3

*E. COLI* 987P FIMBRIAE FORMATION

*E coli*, the causative organism of piglet enterotoxic diarrhea as well as other intestinal diseases in porcine and other human and animal species, produce a fimbria, 987P, which is a secreted virulence determinant required by the bacteria for colonization of the intestinal wall. Naturally, the PORE DsbA directs the formation of the correct three-dimensional conformation of fimbria protein 987P.

The gene encoding 987P fimbria was placed into plasmid pDMS8 which was transfected into *E. coli*, strain K12, which naturally produces endogenous Type 1 fimbriae. The transfected bacteria produced both Type 1 and 987P fimbriae. See FIG. 11.

A DsbA– *E. coli* mutant of strain K12 was transfected with the same pDMS8 plasmid containing the gene encoding 987P. The bacteria was incapable of producing both Type 1 and 987P fimbriae. See FIG. 12.

The presence of pilus 987P may be verified by slide agglutination. Antibodies against the pilus are added to a microscope slide containing *E. coli* organisms. If the pilus is present, the bacteria will form a lattice and will appear to clump, whereas no clumping will appear if the pilus is absent. The presence or absence of a pilus can then be confirmed by electron microscopy.

EXAMPLE 4

HAEMOPHILUS INFLUENZAE

The procedures in Examples 1, 2, and 3 are repeated using *Haemophilus influenzae* in place of *V. cholerae* and *E. coli*. *H. influenzae* naturally secretes the protein virulence determinants IgA protease and Protein M antigen.

The *H. influenzae* virulence determinants are found to be secreted in an inactive form following treatment of the bacteria with DTT.

EXAMPLE 5

EFFECT OF LACK OF FUNCTIONAL PORE ON RESISTANCE TO β-LACTAM ANTIBIOTICS

Wild type *E. coli* harboring a β-lactamase encoding plasmid conferring resistance to ampicillin were grown on solid culture medium containing ampicillin (200 μg/ml). Mutant *E. coli*, lacking the ability to synthesize functional DsbA, were grown on identical culture medium. It was observed that mutant colonies grow very slowly and are translucent compared to wild type which grow normally and are opaque.

Similar results are achieved with wild type *V. cholerae* and mutant *V. cholerae* lacking the ability to synthesize functional TcpG.

Similar results are achieved with wild type *H. influenzae* and mutant *H. influenzae* lacking the ability to synthesize functional Por.

EXAMPLE 6

PRODUCTION OF TCPG OVERPRODUCING CLONE

Figure 14:
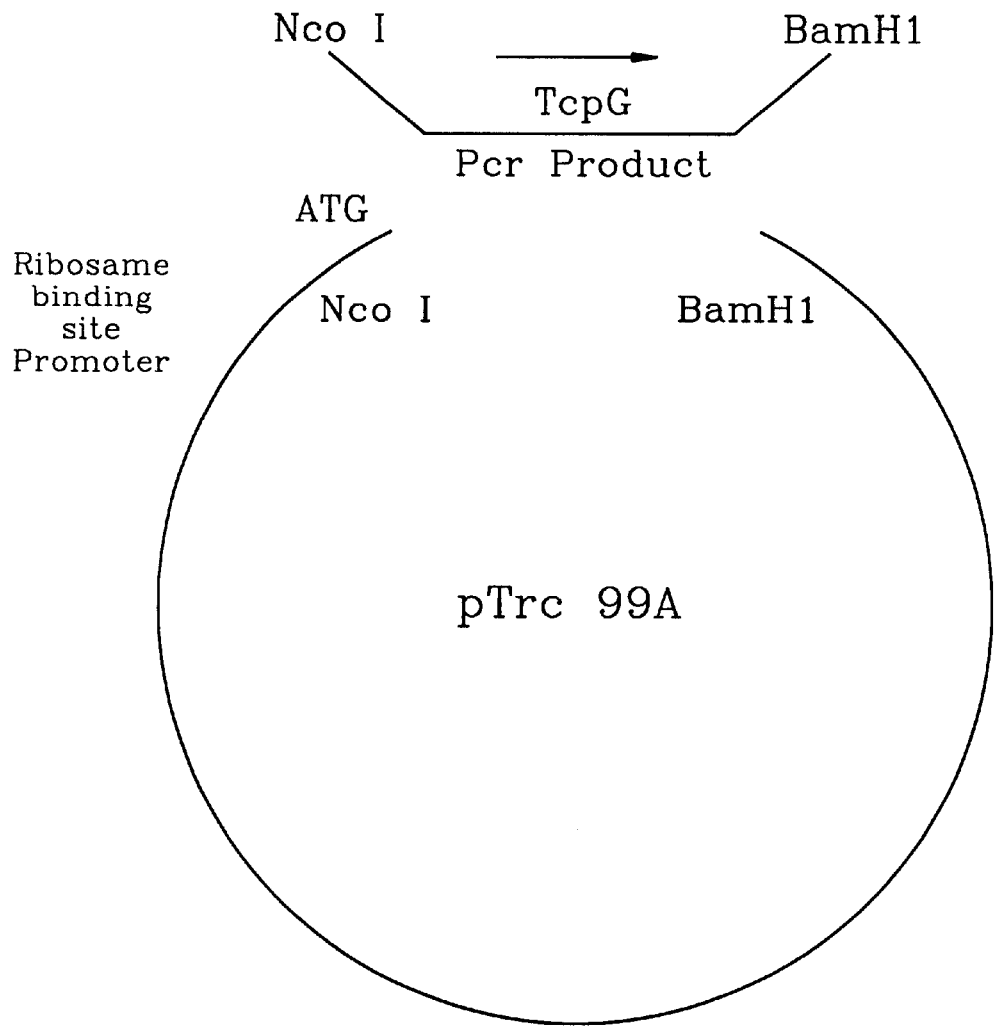

The gene for TcpG was isolated from *V. cholerae* and an NcoI restriction site was inserted at the 5' end and a BamH1 restriction site was inserted at the 3' end thereof. The gene fragment was then inserted downstream adjacent to the strong start ATG codon of a pTrc99A expression vector. See FIG. 14.

The resultant plasmid, pTrc.G1, was inserted into *E. coli*, which were grown overnight in 2 ml LB liquid culture medium. The culture was diluted back 1:10 by placing 0.5 ml of the culture medium containing the bacteria into 4.5 ml of LB medium. The bacteria were allowed to grow for 30 minutes, at which time the trc promoter of the plasmid was induced by adding 0.25 ml of 0.1 mM isopropyl-β-D-thiogalactoside (IPTG). The bacteria were then harvested after about 2.5 to 3 hours.

The cells were spun down for 1 to 2 minutes at 10,000×G and then resuspended in 100 μl of PBS. In order to cause the cells to break open and become spheroplasts, 25 μl of polymyxinB/PBS was added and the bacterial suspension was incubated on ice for 10 minutes. The mixture was spun for 10 minutes at 10,000×G and the supernatant, containing the periplasmic contents including TcpG, was saved. The TcpG was then isolated using standard techniques, such as column separation. Similar results are achieved when *V. cholerae* and *H. influenzae* are transformed with plasmid pTrc.G1.

Other genes, like DsbA and Por, can likewise be overexpressed in a similar manner.

As will be apparent to those skilled in the art, in light of the foregoing description, many modifications, alternations and substitutions are possible in the practice of this invention without departing from the spirit or the scope thereof.

What is claimed is:

1. A method for producing a recombinant protein comprising transforming a host bacterium with a first gene encoding a recombinant protein, transforming said host bacterium with a second gene encoding a bacterial periplasmic protein selected from the group consisting of Por, TcpG, and DsbA, and culturing said host bacterium to produce said recombinant protein, which periplasmic protein catalyzes the formation of disulfide bonds between cysteine residues, wherein said host bacterium is selected from the group consisting of *E. coli, Haemophilus influenzae, Salmonella typhimurium, Bacillus brevis*, Legionella, *Erwinia chryantum*, Streptococcus, and Staphylococcus.

2. The method of claim 1 wherein the periplasmic protein is TcpG from *Vibrio cholerae*.

3. The method of claim 1 wherein the periplasmic protein is DsbA.

4. The method of claim 1 wherein the periplasmic protein is Por.

5. The method of claim 1 wherein the expression of the recombinant protein and the expression of the bacterial periplasmic protein are under the control of a single promoter.

6. The method of claim 5 wherein the promoter is inducible.

7. The method of claim 1 wherein the recombinant protein and the bacterial periplasmic protein are under the control of more than one promoter.

8. The method of claim 1 wherein the recombinant protein is a bacterial protein.

9. The method of claim 1 wherein the recombinant protein is a non-bacterial protein.

10. A method for producing a recombinant protein comprising inserting a first nucleic acid sequence under the control of a promoter into the genome of a host bacterium, inserting into said host genome a second nucleic acid sequence under the control of a promoter, which second nucleic acid sequence encodes a bacterial periplasmic enzyme which catalyzes the formation of disulphide bonds between two cysteine residues, which bacterial periplasmic enzyme is selected from the group consisting of Por, TcpG, and DsbA, and co-expressing the first and second nucleic acid sequences, wherein said host bacterium is selected from the group consisting of *E. coli, Haemophilus influenzae, Salmonella typhimurium, Bacillus brevis*, Legionella, *Erwinia chrysantum*, Streptococcus, and Staphylococcus.

11. The method of claim 10 wherein the periplasmic enzyme is TcpG from *Vibrio cholerae*.

12. The method of claim 10 wherein the enzyme is DsbA.

13. The method of claim 10 wherein the enzyme is Por.

14. The method of claim 10 wherein the first and second nucleic acid sequences are under the control of the same promoter.

15. The method of claim 14 wherein the promoter is inducible.

16. The method of claim 10 wherein the first and second nucleic acid sequences are under the control of more than one promoter.

17. The method of claim 10 wherein the first nucleic acid sequence encodes a bacterial protein.

18. The method of claim 10 wherein the first nucleic acid sequence encodes a non-bacterial protein.

* * * * *